United States Patent [19]

Rusz et al.

[11] Patent Number: 4,770,168
[45] Date of Patent: Sep. 13, 1988

[54] ELECTRICALLY CONTROLLABLE ANESTHESIA VAPORIZER

[75] Inventors: Tibor Rusz, 1508 Tejana Mesa Pl., Albequerque, N. Mex. 87112; W. Stetson Hallowell, Richmond, Mass.

[73] Assignee: Tibor Rusz, Albuquerque, N. Mex.

[21] Appl. No.: 809,251

[22] Filed: Dec. 16, 1985

[51] Int. Cl.[4] .......................................... A61M 16/00
[52] U.S. Cl. ......................... 128/203.12; 128/203.14; 128/203.27
[58] Field of Search ...................... 128/203.12, 203.14, 128/203.25, 203.26, 203.27, 203.28, 204.14, 204.72, 200.11, 200.14, 204.71, 204.17, 205.18, 205.13, 204.13

[56] References Cited

U.S. PATENT DOCUMENTS

| 2,872,167 | 2/1959 | Pratt ................................ 128/203.12 |
| 4,127,121 | 11/1978 | Westenskow et al. .......... 128/203.14 |
| 4,150,670 | 4/1979 | Jewett et al. .................... 128/204.72 |
| 4,345,612 | 8/1982 | Koni et al. ....................... 128/203.14 |
| 4,434,790 | 3/1984 | Olesen ............................ 128/200.14 |
| 4,576,159 | 3/1986 | Hahn et al. ..................... 128/203.14 |
| 4,611,590 | 9/1986 | Ryschka et al. . |

FOREIGN PATENT DOCUMENTS

| 3401923 | 8/1985 | Fed. Rep. of Germany ....................... 128/203.12 |
| 57924 | 9/1967 | German Democratic Rep. ................................ 128/203.25 |
| 2146903 | 5/1985 | United Kingdom ........... 128/203.12 |
| 2150034 | 6/1985 | United Kingdom ........... 128/203.12 |

OTHER PUBLICATIONS

Coles et al., "Computer Control of Respiration and Anaesthesia", Medical and Biomedical Engineering, May 1973.

Primary Examiner—Edward M. Coven
Assistant Examiner—K. M. Reichle
Attorney, Agent, or Firm—Arthur K. Hooks

[57] ABSTRACT

A vaporizer has a main conduit supplied at an inlet end by a carrier gas of oxygen and nitrous oxide having a constant flow rate. The outlet end of the conduit is connected to the breathing system of a patient. A series circuit with an input end connected to a proximal port in the conduit includes a check valve, a chamber in which anesthetic vapor is maintained in saturation and a positive displacement pump driven by an electrical motor for pumping the vapor-saturated gas at a rate that is only a function of an electrical signal applied to the motor. The output of the pump is connected to a distal port of the conduit. More than one such chamber may be provided, each containing a different liquid anesthetic, and any one being connected into the circuit by means of a selector valve.

8 Claims, 3 Drawing Sheets

ELECTRICALLY CONTROLLABLE ANESTHESIA VAPORIZER

BACKGROUND OF THE INVENTION

This invention relates to an anesthesia vaporizer for introducing anesthetic vapor into the breathing gas supplied by an anesthesia machine to a patient undergoing surgery, and more particularly relates to such a vaporizer capable of being electrically controlled.

A typical anesthetic vaporizer 10 of the prior art is illustrated in FIG. 1, connected to a patient's breathing-system 20. The output of a pulmonary ventilator 12 is also connected, via an absorber head 14 and check valves 16 and 18, to the patient's breathing system 20. Such a ventilator 12 and absorber head 14 is described in more detail in my copending application Ser. No. 685,906 filed Dec. 24, 1984. In addition to anesthetic, muscle relaxants or paralyzing drugs are commonly dispensed to most patient's undergoing surgery. A paralyzed patient requires forced breathing assistance by a pulmonary ventilator. Depending upon the needs of the particular patient however, an anesthesia vaporizer may be used with or without a pulmonary ventilator.

In the prior art vaporizer 10, a carrier gas 22, usually made up of oxygen and nitrous oxide is transmitted through a conduit 24 that includes a restrictor portion 26. A central portion of the conduit 24 including restrictor portion 26 is bypassed, i.e. paralleled, by a long pipe shown as a coil of pipe 28 and a vaporizing chamber 30. Chamber 30 may contain a heated reservoir of liquid anesthetic. In the space above the liquid, the atmosphere of carrier gas 22 is saturated with anesthetic, which saturated gas enters pipe 24 downstream of the restrictor 26.

The concentration of anesthetic in the carrier gas exiting the pipe 24 varies greatly as the pressure at the patient's breathing system varies because the breathing system pressure variations are also reflected at the output of the pipe 24 in the vaporizer.

At the time of high pressure in the breathing cycle, the anesthetic leaves the vaporizer at a low rate. At a subsequent moment of low pressure in the breathing system a glut of anesthetic is introduced into the absorber head and will be delivered in a concentrated pulse to the patient's breathing system in the next inspiratory period. This problem stems from the fact that the flow rate of the carrier gas through the vaporizing chamber 30 is affected by the patient's breathing-system pressure. The saturated vapor concentration is also a function of the temperature. Furthermore, the concentration of anesthetic vapor in the carrier gas is a function of the carrier gas flow rate. A bypass valve 31 is adjusted by the anesthesiologist to establish and maintain the desired average concentration of anesthetic vapor in the carrier gas as is measured and displayed by the vapor concentration monitor 32.

It is an object of this invention to provide an anesthesia vaporizer capable of producing a substantially constant anesthetic concentration regardless of breathing pressure and temperature variations.

It is a further object of this invention to provide such an anesthesia vaporizer wherein the anesthetic concentration is controllable by an electrical signal.

SUMMARY OF THE INVENTION

An electrically controllable anesthesia vaporizer is described for controlling the rate of anesthetic vapor that is introduced into a stream of carrier gas flowing at a constant rate through the vaporizer. It is comprised of a conduit for conveying a stream of carrier gas from a constant-flow-rate source of carrier gas to the patient's breathing system.

A closed container holds a liquid anesthetic and has an inlet port connected to a proximal port in the conduit. An electric-motor-driven, positive-displacement pump is connected between an outlet port of the vaporizer container and a distal port of the conduit so that some of the carrier gas from the source bypasses a central portion of the conduit between a proximal and distal port. Alternatively, an entirely separate source of carrier gas may be connected to the inlet port of the vaporizer. In fact, the speed at which the motor and thus the positive displacement pump operate determines exactly the flow rate of the bypassing carrier gas. Since the saturation vapor pressure of a liquid anesthetic is not a function of pressure, the flow rate of anesthetic vapor into the carrier gas is directly proportional to the speed of the motor, independent of pressure variations in the patient's breathing system. In this way the concentration of the anesthetic vapor is fixed in the carrier gas as it exits the vaporizer outlet at an amount that is linearly proportional to the motor and pump speed only.

DESCRIPTION OF THE PREFERRED EMBODIMENTS

Figure 1:
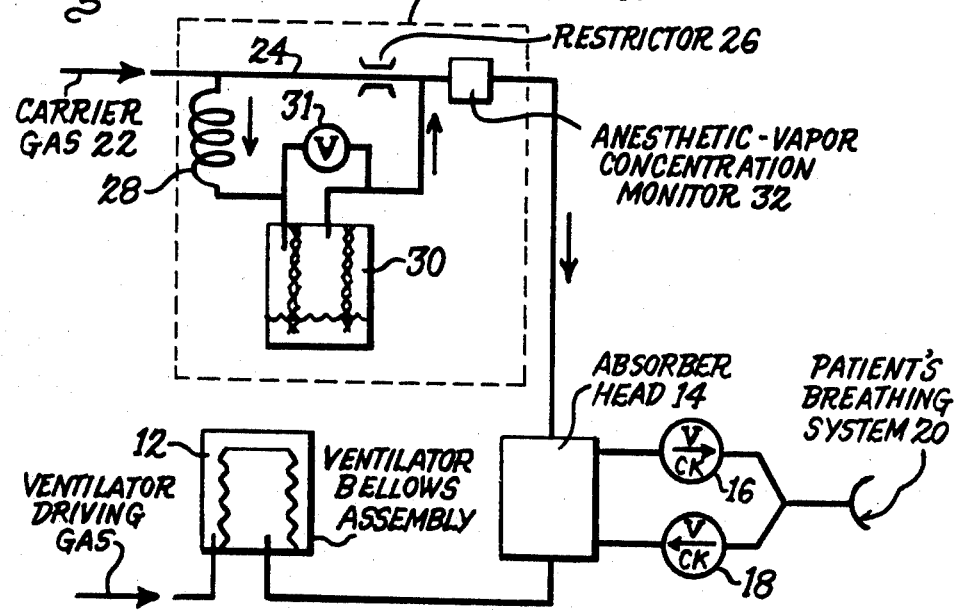
FIG. 1 shows a diagram of an anesthesia vaporizer of the prior art.
Figure 2:
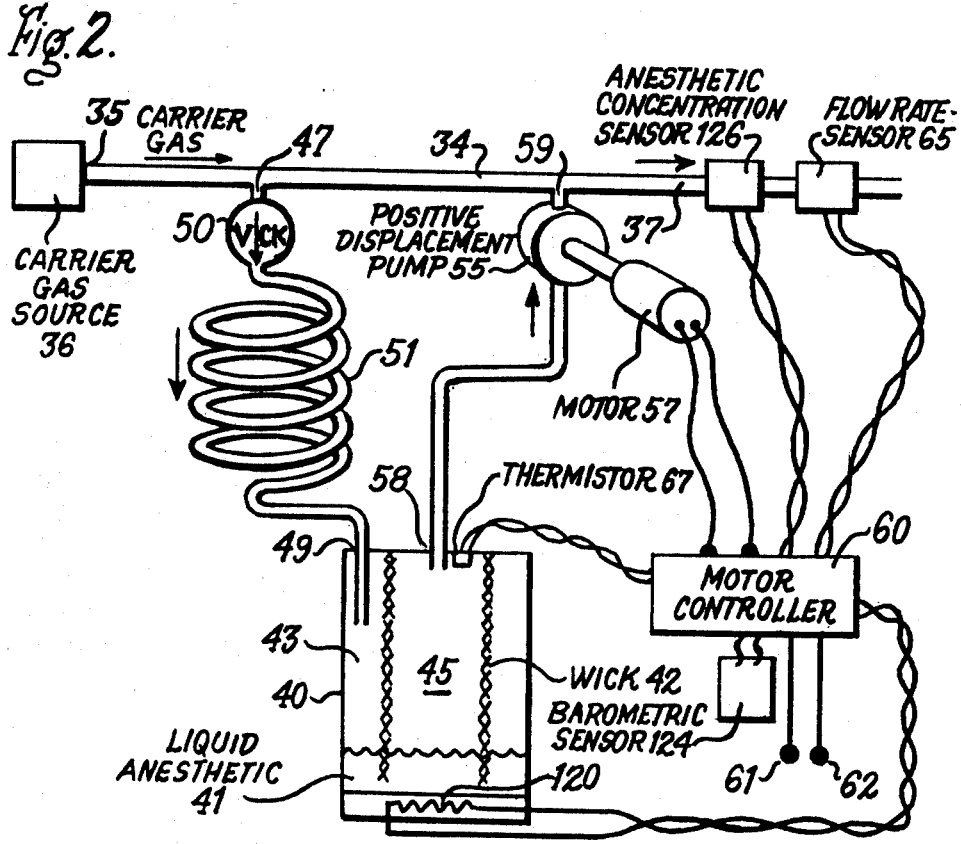
FIG. 2 shows a diagram of an anesthesia vaporizer of this invention.

Referring to FIG. 2, the pipe 34 has an inlet end 35 connected to the output of a carrier gas source 36 of constant-flow rate. The source 36 may include tanks of high pressure, e.g. 50 p.s.i., gas passed through a standard rotameter for setting and maintaining a flow rate. The carrier gas may be a mixture of $N_2O$ and $O_2$ with a flow rate between 0.2 and 15 liters per minute and is set by the anesthesiologist to meet the needs of the particular patient. The pipe 34 has no restictor between inlet end 35 and outlet end 37, but as will be seen, a restrictor there would have essentially no effect in this vaporizer.

A closed container 40 has a bottom portion serving as a reservoir for liquid anesthetic 41. A cylindrical wick 42 is mounted centrally in the container 40 forming in the chamber space above the liquid an upper-outer compartment 43 and an upper-inner compartment 45. A conduit connecting a proximal port 47 in pipe 34 to an inlet port 49 includes a check valve 50 and a long length of tubing 51 in the compact form of a coil. The long tubing 51 like the long pipe 28 in the prior art vaporizer, accounts for the fact that the pressure in pipe 34 varies during each breathing cycle from about ambient to about 1 p.s.i. higher. The diffusion of anesthetic vapor against the gas flow in pipe 51, introduces little vapor into pipe 34 during moments of low pressure because of the long path it must travel. The check valve 50 stops backward flow (upward as shown) of the carrying gas in pipe 51 that may occur momentarily at the very lowest pressures during a breathing cycle, thus eliminating another means of introducing anesthetic vapor into pipe 34 via proximal port 47. The check valve 50 may be supplanted by any other means for providing an effective barrier to this reverse flow of anesthetic vapor by diffusion. In the extreme case an entirely separate source of carrier gas may be connected to the inlet port of the vaporizer.

Carrier gas from the coiled pipe 51 enters the upper-outer compartment 43 of chamber 40 via inlet port 49. From there it passes through the wick 42 moving into the upper-inner compartment 45. In compartment 45 vapor is maintained at the saturation level. For the liquid anesthetic, halothane, it amounts to 243 mm Hg vapor pressure at 20° C.

The vapor pressure of liquid anesthetic is not a function of pressure in the vaporizer chamber 40. It is however a function of temperature. In the prior art, the vapor concentration at the vaporizer output is typically maintained constant by a temperature responsive mechanical means for partially closing the outlet port of the vapor container 30 as the temperature rises.

A central element in the vaporizer of this invention is a positive displacement pump 55, i.e. a pump having a piston or other means that produces at the output a fixed volume of gas each stroke, or cycle. Any positive displacement pump having an appropriate volume rate delivery range for the medical procedure contemplated will be suitable. A driving motor 57 may be a stepping motor, a DC motor or any motor capable of driving at a speed that is under the control of an electrical signal. Thus for a stepping motor the gas flow through-put rate will be a function of the frequency of the control signal, whereas a DC motor responds to the amplitude of the electrical energizing signal to the pump.

For most situations, a suitable pump is Model RP-B-2 made by Fluid Metering, Inc., Oyster Bay, N.Y. This positive displacement pump is rated for a normal speed of 2800 strokes a minute delivering an output flow of 1700 ml/min. The pump may be driven by a DC motor capable of speeds of 2800 strokes down to about 400 strokes per minute under control of a conventional DC motor controller 60 that provides a motor speed that is directly related to the amplitude of a voltage applied to the controller at terminals 61 and 62. Some applications, however, may require a gas delivery rate of as much as 4 liters/min. in which case a positive displacement pump with a larger capacity will be required. When the motor 57 is a stepping motor, the electrical signal produced at the motor input may be derived from a voltage controlled oscillator (VCO) 64 that is included in the controller 60.

In order to further minimize variations of anesthetic vapor at the conduit-output end 37, the volume of the connecting pipe 59 need be kept as small as possible, and at least less than 10 milliliters.

One use to which the electrically controllable vaporizer of this invention is particularly well adapted arises from the frequent need for the anesthesiologist to change the rotameter monitored flow rate of carrier gas, which further leads him to also adjust the rate at which anesthetic is being introduced to the carrier gas so as to maintain the desired concentration. Now it is possible for the first time to measure the flow rate using a flow rate transducer 65 that provides an electrical output which automatically through the motor controller 60 maintains the anesthetic concentration in the carrier gas at a desired level.

It is also possible now to place a thermistor 67, or other temperature-to-electrical signal transducer in the compartment 45, connecting the thermistor 67 to the controller 60 and compensating for the change in saturation vapor pressure of the anesthetic as a function of temperature. For higher temperatures, the saturation vapor pressure goes up and the vapor concentration increases in compartment 45. Thus the controller may slow the pump to maintain to a high degree of accuracy a constant vapor concentration in the main stream of carrier gas from the vaporizer. This feature is preferably employed in addition to designing the motor controller 60 also to power the heater 120 and coarsely maintain thereby the anesthetic 41 at about 25° C.

The electrically controllable vaporizer of this invention is uniquely capable of establishing and maintaining the concentration of anesthetic vapor in the stream of carrier gas to an accuracy of ±0.1%.

Figure 3:
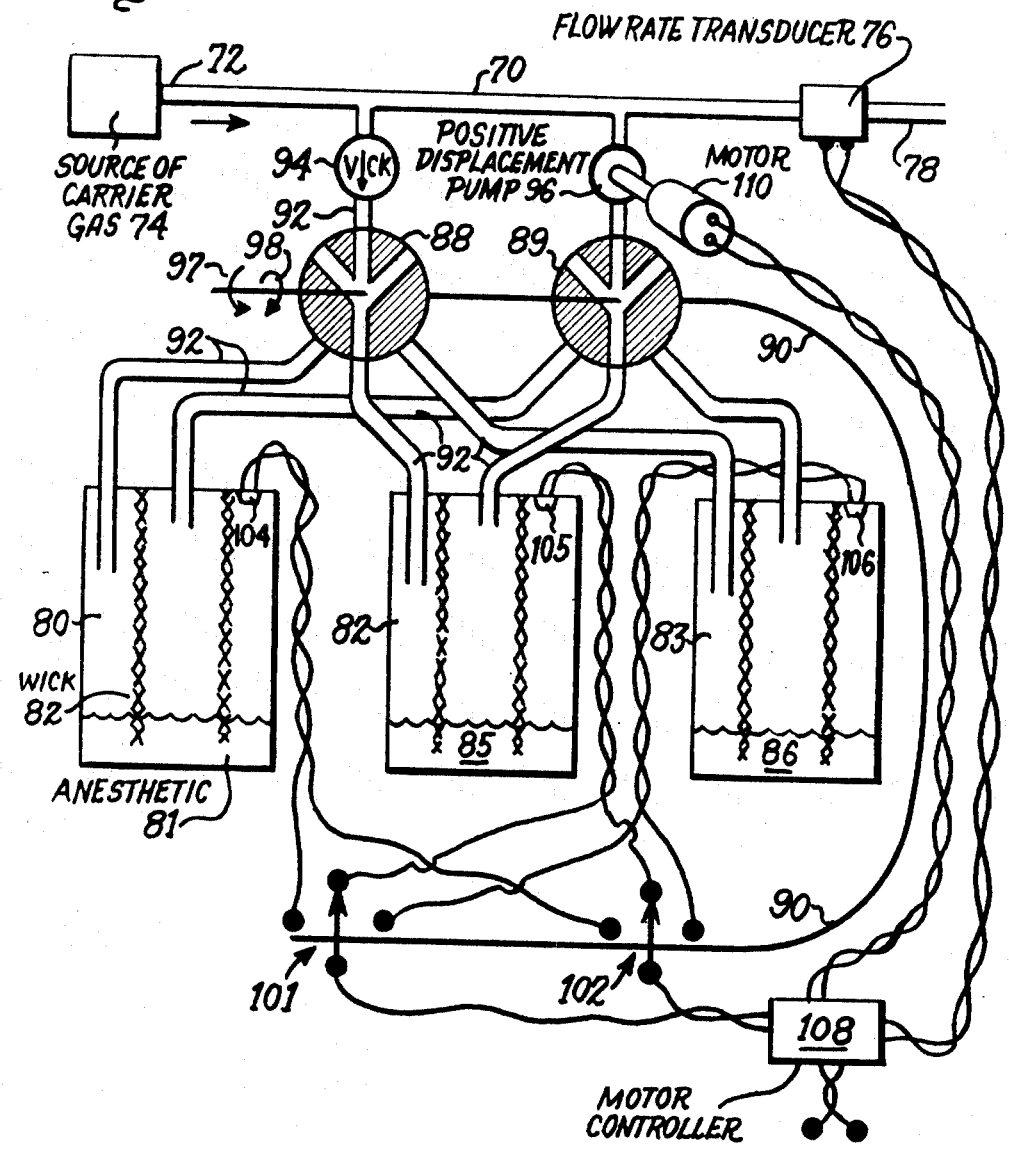
FIG. 3 shows a diagram of another anesthesia vaporizer of this invention.

A second preferred embodiment is illustrated in FIG. 3. The conduit 70 has an inlet end 72 connected to the output of a source 74 of pressurized carrier gas. A flow-rate transducer 76 is connected near the conduit end 78 which may be connected to a patient's breathing system (not shown).

A first closed container 80 has a bottom portion serving as a reservoir for a first anesthetic liquid 81. A cylindrical wick 82 is mounted centrally in the container 80, similar to the wick 42 that is centrally located in the container 40 of FIG. 2. Two additional identical containers 82 and 83 are also provided containing different liquid anesthetic liquids 85 and 86. First and second multi-position valves 88 and 89 are mechanically ganged by a shaft 90, are shown positioned to connect via a network of pipes 92 the check valve 94 to the inlet compartment of container 82 and to connect the inlet port of the positive displacement pump 96 to the outlet chamber of container 82. By turning the shaft 90 counter clockwise as indicated by arrow 97, the container 83 is connected from the check valve 94 to the pump 96. Turning the shaft counter clockwise, as indicated by arrow 98, connects anesthetic container 80 between the check valve 94 and pump 96.

Also ganged to shaft 90 are two single-pole triple-throw switches 101 and 102 so that the thermistor among those 104, 105 and 106 respectively mounted in containers 80, 82 and 83, corresponding to the container connected between valve 94 and pump 96 is connected to the motor controller 108. Motor controller 108 controls the pump motor 110 and senses the output voltage of the flow rate transducer 76. The anesthesiologist is thus enabled to switch instantly from one anesthetic to another by manipulating the valve-switch shaft 90.

Thus relative to the system of FIG. 2, the vaporizer of FIG. 3 has a main anesthetic container 80 and additionally has at least another closed container 82 both having an anesthetic reservoir and inlet and outlet ports. This vaporizer further comprises a first multi-position valve 88 for when in one position connecting the inlet port of said main container 80 to the source 74 of carrier gas and when in the position shown connecting the inlet port of container 82 to the source 74 of carrier gas, and a second multi-position valve 89 for when in the one position connecting the outlet port of the main container to the inlet side of the pump 96 and when in the shown position connecting port of the container 82 to the inlet side of said pump 96, and the multi-position valves 88 and 89 being ganged so that both are in the one position or are both in the shown position.

Some anesthetia vaporizers of the prior art that are adjusted at one elevation to provide a certain concentration of vapor pressure in a given carrier gas stream, will at a higher elevation produce a greater anesthetic vapor concentration. This is true because the breathing gas is about at ambient pressure while the saturation vapor pressure of an anesthetic is unchanging with ambient pressure, e.g. halothane has a saturation vapor pressure of 243 mm Hg at 20° C. at all altitudes.

In FIG. 2, a barometric pressure to electrical-signal transducer, or sensor 124, is shown connected to the controller 60 which may be programmed to adjust the motor speed and anesthetic flow rate through the pump 55 so as to maintain the anesthetic vapor concentration constant as measured by the concentration analyzer 126. Alternatively, the controller 60 may be programmed with the relationship by which the anesthetic concentration, for the particular anesthetic in use, is dependent upon barometric pressures. In this way the controller 60 can maintain constant the concentration of anesthetic vapor in the carrier gas at all altitudes without feedback from a concentration analyzer (126).

For a given temperature that relationship is $$C' = C (P/P')$$

where C is the wanted anesthetic volume percent set in the vaporizer controller 60, C' is the output concentration in anesthetic volume percent at a different pressure, P is the barometric pressure for which the vaporizer is calibrated and P' is the different barometric pressure for which C' is being established by the vaporizer.

Figure 4:
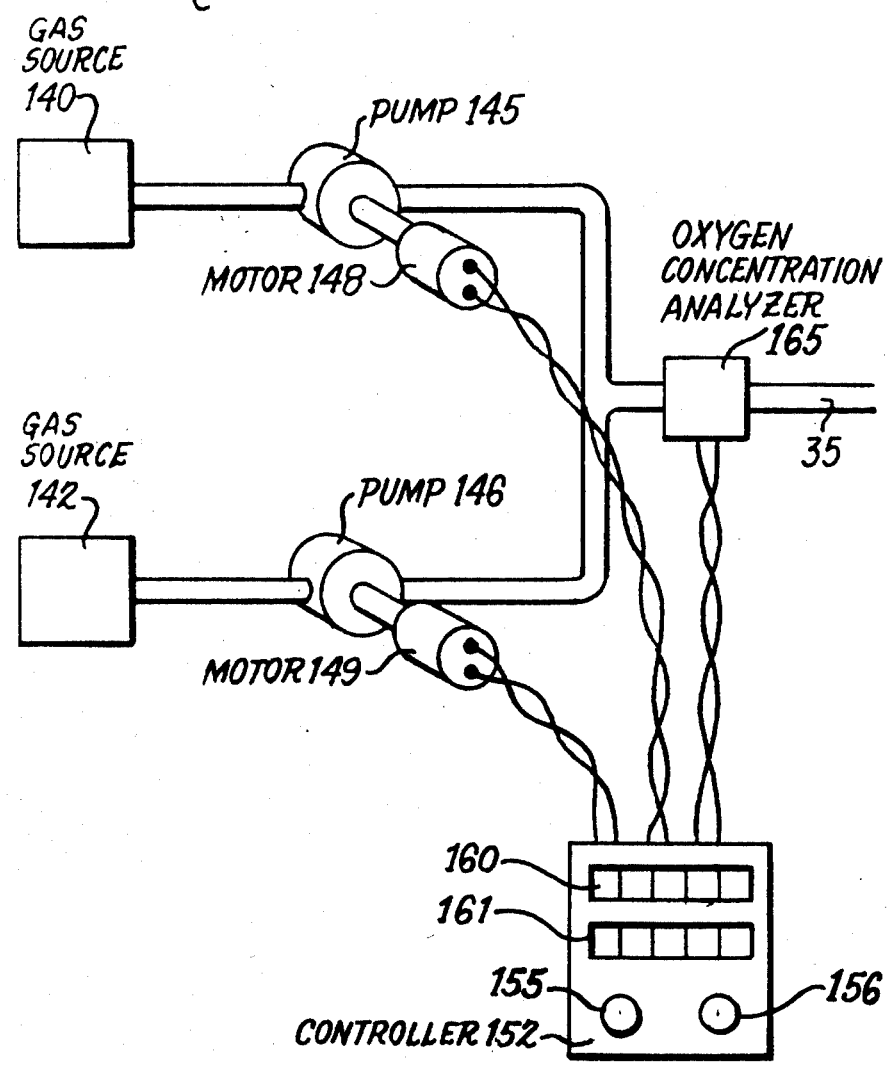
FIG. 4 shows a diagram of an improved carrier gas source that may be connected to a vaporizer of this invention.

The electrically controlled vaporizer of this invention may be supplied by an improved source of driving gas which is illustrated in FIG. 4. Here a source 140 of oxygen and a source of nitrous oxide 142 may simply be a tank of oxygen and a tank of nitrous oxide, respectively. These tanks may contain the gases at over a wide range of pressures. Each source 140 and 142 is connected to a patient's breathing system (not shown), e.g. via a conduit 35, through positive displacement pumps 145 and 146, respectively. These pumps 145 and 146 are driven, respectively by motors 148 and 149 which are electrically powered by the controller 152. Of course more than two gas sources, pumps and motors may be so connected in parallel, for example helium or carbon dioxide may be added.

The controller 152 is for determining the speeds of the motors 148 and 149 and thus the rate of delivery of the oxygen and nitrous oxide respectively in response to instructions given to it by the anesthesiologist via front panel controls 155 and 156. Display windows 160 and 161 on the face of the controller 152 show the ratio of oxygen to nitrous oxide and the flow rate of the mixture. Alternatively the separate flow rates of the two gases may be displayed respectively at windows 160 and 161.

An oxygen concentration monitor 165 provides a signal proportioned to the oxygen concentration in conduit 35. The output signal of monitor 165 is electrically connected to the controller 152 that may contain a microprocessor for determining the ratio of oxygen to nitrous oxide or other gases, and automatically provide at least a minimum percent oxygen, e.g. 25%, in the case the anesthesiologist's instructions would not so provide that minimum acceptable level of life supporting oxygen. It is also easily possible, using the electrically controlled gas sources here, to maintain constant the concentration of oxygen in the mixture, at a preset level by sensing and holding constant the signal from the oxygen concentration analyzer 165. Of course, this carrier gas source like those of the prior art may be used with or without a vaporizer for supplying oxygen to a patient's breathing system.

Thus precise electrical control of composition and flow rate of the carrier gas is provided by the combination of positive displacement pumps and driving motors, which combination is similarly advantageous in the vaporizer of this invention.

What is claimed is:

1. An electrically controllable anesthesia vaporizer for introducing vapor at a controllable rate into a carrier gas stream flowing therethrough comprising:
   (a) a main closed container with an outer wall, said container having in a portion thereof a reservoir for holding a liquid anesthetic, having a chamber means above said reservoir for collecting and containing anesthetic vapor from said liquid anesthetic, and having spaced apart inlet and outlet ports extending through separate portions respectively of said container wall, said inlet port being adapted for connection to a source of a carrier gas;
   (b) a conduit having a source end adapted for connection to another a source of a carrier gas, having a load end adapted for connection to a patient's breathing-system, and having a distal port located in said wall of said conduit near said load end;
   (c) an electric-motor-driven pump assembly comprising a positive displacement pump having an inlet side and an outlet side; and an electric motor mechanically connected to said pump; and
   (d) an outlet connection for connecting said pump between said container outlet port and said distal port of said conduit to introduce the anesthetic vapor into the carrier gas stream flowing in said conduit, when an electrical energizing signal is applied to said motor, and at a rate that is directly related to a parameter of the electrical energizing signal.

2. The vaporizer of claim 1 wherein said connection between said pump and said distal port is short and has a small gas capacity of less than 10 ml to prevent this connection from acting as a large reservoir of anesthetic vapor that can discharge abruptly into the patient's breathing system at the beginning of each inspiratory breathing period.

3. The vaporizer of claim 1 wherein said motor is a DC motor of the kind having a speed that is directly related to the DC amplitude parameter of the applied energizing signal.

4. The vaporizer of claim 1 wherein said motor is a stepping motor of the kind having a rotor that rotates through an angle that is directly proportional to the number of AC pulses parameter of the appied electrical energizing signal.

5. The vaporizer of claim 1 wherein said closed container additionally has a wick one end of which is submersed in said liquid anesthetic and the other end of which extends upwardly into said chamber means.

6. The vaporizer of claim 1 additionally comprising a wick means in said reservoir wherein said wick means is for extending into said container to serve as a barrier in said chamber means and to divide said chamber means into two compartments above said reservoir, said inlet port being in an outer wall of a first of said compartments and said outlet port being in an outer wall of the second of said compartments.

7. The vaporizer of claim 1 additionally comprising at least another closed container having a liquid anesthetic reservoir, and inlet and outlet ports; a first multi-position valve connected to said inlet port of said main container and to said inlet port of said another container, adapted for when in position A connecting said inlet port of said main container to a source of carrier gas and when in position B connecting said inlet port of a source of carrier gas; and a second multi-position valve connected to said outlet port of said main container, to said pump and to the outlet port of said another container, for when in position A connecting said outlet port of said main container to said pump and when in position B connecting the outlet port of said another container to said inlet side of said pump, and said multi-position valves being ganged so that both are in positions A or are both in positions B.

8. In an anesthesia vaporizer of the kind including a conduit adapted for connecting a source of a carrier gas to the breathing system of a patient, said conduit having a port in a side wall thereof through which anesthetic vapor may be introduced, and including a main closed containing means for holding a quantity of a liquid anesthetic, for vaporizing the anesthetic, for admitting a carrier gas to mix with the anesthetic vapor, and for maintaining the condition of anesthetic vapor saturation in the admitted carrier gas, the improvement comprising:

an electric-motor-driven pump assembly, including a motor and a positive displacement pump mechanically connected to said motor, said pump being connected between said containing means and said port in said conduit for conveying, when an electrical energizing signal is applied to said motor, the anesthetic vapor saturated carrier gas from said containing means to said conduit at a rate that is directly related to a parameter of the electrical energizing signal.

* * * * *